(12) United States Patent
Jansen et al.

(10) Patent No.: US 11,246,497 B2
(45) Date of Patent: Feb. 15, 2022

(54) METHOD AND COMPUTER SYSTEM FOR PROCESSING A HEART SENSOR OUTPUT

(71) Applicants: Jozef Reinier Cornelis Jansen, Noordwijkerhout (NL); Johannes Jacobus Schreuder, Leiden (NL)

(72) Inventors: Jozef Reinier Cornelis Jansen, Noordwijkerhout (NL); Johannes Jacobus Schreuder, Leiden (NL)

(*) Notice: Subject to any disclaimer, the term of this patent is extended or adjusted under 35 U.S.C. 154(b) by 378 days.

(21) Appl. No.: 15/575,120

(22) PCT Filed: Jun. 4, 2015

(86) PCT No.: PCT/NL2015/050403
§ 371 (c)(1),
(2) Date: Nov. 17, 2017

(87) PCT Pub. No.: WO2016/195477
PCT Pub. Date: Dec. 8, 2016

(65) Prior Publication Data
US 2018/0146864 A1    May 31, 2018

(51) Int. Cl.
*A61B 5/02* (2006.01)
*A61B 5/0215* (2006.01)
(Continued)

(52) U.S. Cl.
CPC ........ *A61B 5/0215* (2013.01); *A61B 5/02141* (2013.01); *A61B 5/686* (2013.01); *G16H 40/63* (2018.01); *G16H 50/50* (2018.01); *A61M 60/135* (2021.01); *A61M 60/148* (2021.01); *A61M 60/40* (2021.01); *A61M 60/50* (2021.01)

(58) Field of Classification Search
None
See application file for complete search history.

(56) References Cited

U.S. PATENT DOCUMENTS

2009/0177279 A1* 7/2009 Luciano .............. A61M 1/1072
623/11.11
2012/0053918 A1    3/2012 Taylor
(Continued)

FOREIGN PATENT DOCUMENTS

JP    2013534154 A    9/2013
WO   2002028280 A1   4/2002
(Continued)

OTHER PUBLICATIONS

Nagai, Y. et al. "Associations of aortic Windkessel function with age, gender and cardiovascular risk factors," Ultrasound in Medicine and Biology, New York, NY (Sep. 1, 2001), 27(9): 1207-1210.
(Continued)

*Primary Examiner* — Rex R Holmes
(74) *Attorney, Agent, or Firm* — Gregory W. Smock

(57) ABSTRACT

The disclosure relates to a method and system for processing a heart sensor output, wherein a blood flow and a simulated aortic blood pressure are derived from a sensed blood pressure using an arterial flow model and values for arterial flow parameters. The simulated aortic blood pressure is matched to a part of the sensed blood pressure in the cardiac cycle by manipulating at least one of the values for the arterial flow parameters of the arterial flow model.

20 Claims, 10 Drawing Sheets

(51) Int. Cl.
*A61B 5/021* (2006.01)
*G16H 50/50* (2018.01)
*A61B 5/00* (2006.01)
*G16H 40/63* (2018.01)
*A61M 60/40* (2021.01)
*A61M 60/50* (2021.01)
*A61M 60/135* (2021.01)
*A61M 60/148* (2021.01)

(56) References Cited

U.S. PATENT DOCUMENTS

| | | | |
|---|---|---|---|
| 2014/0275886 A1 | 9/2014 | Teixeira | |
| 2015/0018632 A1* | 1/2015 | Khair | A61B 5/026 |
| | | | 600/301 |
| 2015/0045644 A1 | 2/2015 | Comaniciu et al. | |

FOREIGN PATENT DOCUMENTS

| | | |
|---|---|---|
| WO | 2012021307 A2 | 2/2012 |
| WO | 2013138428 A1 | 9/2013 |
| WO | 2015006191 A1 | 1/2015 |

OTHER PUBLICATIONS

PCT International Search Report dated Jan. 27, 2016, in application No. PCT/NL2015/05043.

PCT Written Opinion dated Jan. 27, 2016, in application No. PCT/NL2015/050403.

Wang, J.J.: "Systemic venous circulation. Waves propagating on a windkessel: relation of arterial and venous windkessels to systemic vascular resistance." American Journal of Physiology: Heart and Circulatory Physiology (Aug. 12, 2005), 290(1): H154-H162.

Wang, Jiun-Jr. et al. "Time-domain representation of ventricular-arterial coupling as a windkessel and wave system," American Journal of Physiology: Heart and Circulatory Physiology (Dec. 12, 2002), 284(4): H1358-H1368.

Westerhof, Nico et al. "The arterial Windkessel," Medical & Biological Engineering & Computing, Springer, Berlin, DE (Jun. 10, 2008), 47(2): 131-141.

Jansen, Jos R.C. et al. "Determination of cardiac output from pulse pressure contour during intra-aortic balloon pumping in patients with low ejection fraction," Journal of Clinical Monitoring and Computing (2020), 34(2): 233-243.

* cited by examiner

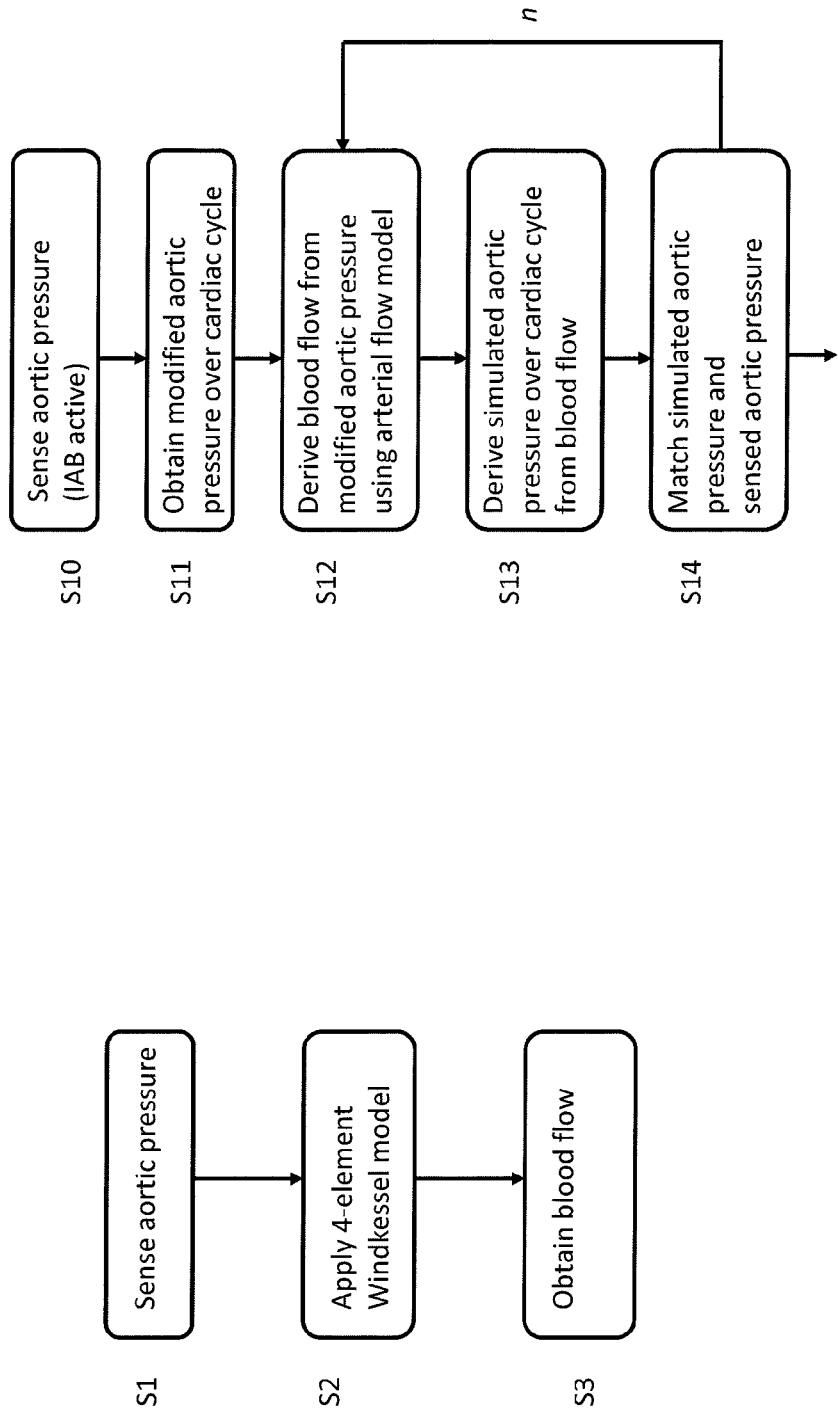

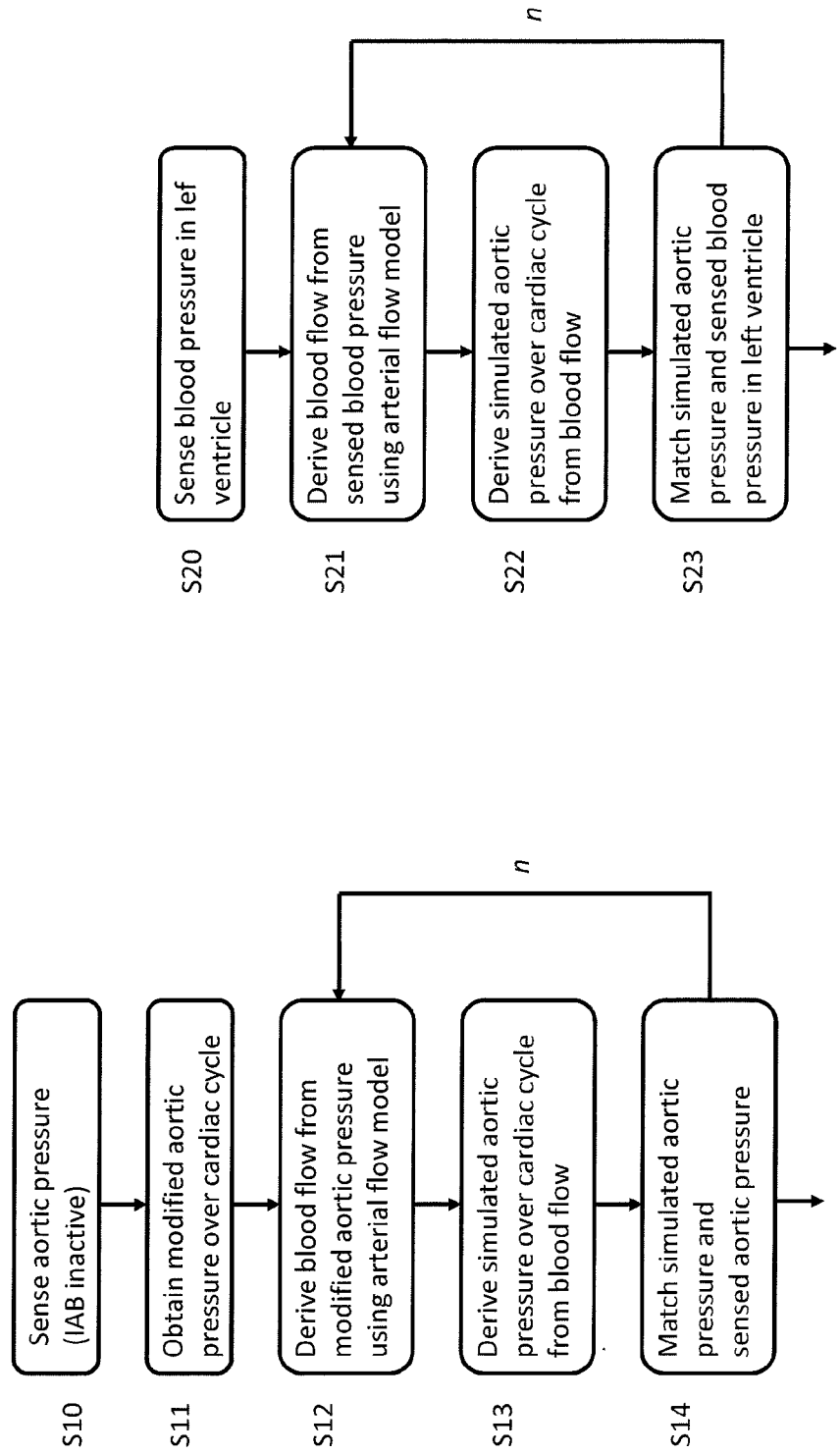

METHOD AND COMPUTER SYSTEM FOR PROCESSING A HEART SENSOR OUTPUT

This patent document is a national stage application under U.S.C. § 371 of PCT Application Serial No. PCT/NL2015/050403, filed Jun. 4, 2015, which is incorporated herein by reference in its entirety.

FIELD OF THE INVENTION

The invention relates to a method and system for processing a heart sensor output. More specifically, the invention relates to a method and system for processing a heart sensor output, wherein the heart sensor output relates to the pressure in a heart related cavity, such as the aorta or the left ventricle of a heart, over a cardiac cycle.

BACKGROUND

Blood pressure and flow in the aorta of a patient define the load of the left ventricle of the heart of the patient. It is known in practice to measure maximal systolic pressure, minimal diastolic pressure and mean arterial pressure. However the hemodynamic state (load) may change rapidly. Systems that measure blood pressure and blood flow on an interval base (such as the upper arm Riva-Rocci method for pressure and thermodilution for cardiac output are unsuitable to monitor critical ill patients.

Thus methods and apparatus have been developed for continuous monitoring of arterial blood pressure and blood flow. To continuously monitor arterial pressure, a pressure line connected to a pressure transducer is typically introduced into an artery and after some signal processing a continuous pressure signal and derived values of systolic, diastolic and mean pressure are presented on a patient monitor.

In critically ill patients, the heart is often supported with a so-called heart assist device, e.g. an intra-aortic balloon pump (IABP). In this procedure, a catheter equipped with an intra-aortic balloon is positioned in the upper part of the aorta. During early diastole of a cardiac cycle, this balloon is inflated and late in diastole of the cardiac cycle this balloon is emptied. The heart assist device may or may not be operative during each cardiac cycle.

The operation of the heart assist device, however, disturbs accurate continuous monitoring of the arterial blood pressure. This hampers obtaining accurate monitoring results for arterial blood pressure, blood flow and other parameters derived from the monitoring results. In one example, the blood pressure monitoring results are needed as an input for controlling the heart assist device (in particular, the times for inflating and deflating the balloon).

SUMMARY

It is an object of the invention to obtain continuous heart monitoring results irrespective whether the heart assist device is operative or not.

To that end, one aspect of the present disclosure pertains to a method for processing a heart sensor output, wherein the heart sensor output comprises a sensed blood pressure over a cardiac cycle of a heart.

The method also comprises deriving blood flow from the sensed blood pressure or a derivative thereof by using an arterial flow model and setting one or more values for arterial flow parameters for the arterial flow model. One arterial flow model known for real-time derivation of blood flow from blood pressure data in general comprises the Windkessel arterial flow model.

Then, a simulated aortic blood pressure is derived from the derived blood flow using the same arterial flow model and the set values for the arterial flow parameters. The simulated aortic blood pressure is matched to a part of the sensed blood pressure or the derivative thereof in the cardiac cycle by manipulating at least one of the values for the arterial flow parameters of the arterial flow model.

The steps of the method may be repeated to improve the match between the simulated aortic blood pressure and the (part of the) sensed blood pressure or the derivative thereof.

The matching operation may involve minimizing the difference between the simulated and the sensed blood pressure or the derivative thereof, e.g. at the end of the diastole of the cardiac cycle.

The result of the processing of the sensed aortic blood pressure may be used as an input for another device, e.g. for controlling another device, such as a patient monitoring device or a heart assist device. For example, a beat-to-beat aortic pressure curve may be obtained that is compensated for the effect of a heart assist device. Furthermore, the variation of the value of one or more arterial flow parameters can be monitored.

Other aspects of the disclosure relate to a computer program or suite of computer programs for performing the disclosed method and to a non-transitory record carrier carrying the computer program.

Yet another aspect of the disclosure involves a computer system comprising a processor and storage means storing instructions or configured for storing instructions for processing a heart sensor output as defined herein.

By generating the aortic blood pressure from the computed blood flow over a cardiac cycle by introducing the blood flow, computed with the arterial flow model using the sensed blood pressure, back into the arterial flow model, the aortic blood pressure over the cardiac cycle can be obtained by tuning at least one of the arterial flow parameters to match the generated aortic blood pressure with a part of the undisturbed sensed aortic blood pressure. The heart sensor output relates to the pressure in a heart related cavity, such as the aorta or the left ventricle of a heart, over a cardiac cycle. The generated aortic pressure is not affected by eventual operation of a heart assist device in the aorta during one or more cardiac cycles.

A still further aspect of the disclosure involves a method for processing a heart sensor output when processed by the processor, wherein the heart sensor output comprises a sensed aortic blood pressure and wherein the processing comprises deriving blood flow of the heart using an arterial flow model. The arterial flow model comprises a Windkessel model represented by at least:

a capacitor $C_W$ a resistor $R_p$ connected in parallel to the capacitor $C_W$ a Zener diode $Z_D$ connected in series with the resistor $R_p$ wherein a value of the capacitor $C_W$ is associated with arterial compliance, a value of the resistor $R_p$ is associated with peripheral resistance and a value of the Zener diode $Z_D$ is associated with backpressure of the blood flow.

The arterial flow model may comprise further known elements, such as at least one of a diode D representing the aortic valve of the heart and an electrical impedance $Z_O$ connected in series with the diode and representing the non-linear pressure impedance experienced by the heart.

The method using the Windkessel model comprising the Zener diode may or may not be used in combination with the method of claims 1-13.

The Zener diode accounts for the backpressure of the blood flow described as a waterfall phenomenon by Maas et al. in Anesthesia & Analgesia 2012; 1144:803-810). The backpressure may vary between 0 and 50 mmHg. Inclusion of the backpressure in the Windkessel model improves the accuracy in deriving blood flow. In one disclosed embodiment, the heart related cavity is the aorta and the sensed blood pressure is the sensed aortic blood pressure. The method further comprises the step of obtaining the derivative of the sensed aortic blood pressure by suppressing the sensed aortic blood pressure during a time interval of a diastolic stage of the cardiac cycle. Suppression of the sensed aortic blood pressure may be achieved in various manners, e.g. by setting the sensed aortic blood pressure to zero during the time interval or by ignoring the values of the sensed aortic blood pressure for obtaining the modified aortic blood pressure. The method may e.g. be advantageously applied when the patient has a heart assist device placed in the aorta that is not operative during the cardiac cycle to which the sensed blood pressure relates.

During other cardiac cycles, the heart assist device may be operative. Hence, in one embodiment, the sensed aortic blood pressure is affected by a heart assist device during the time interval of the cardiac cycle. Typically, the time interval during which the heart assist device affects the blood pressure is a time interval during diastole of the cardiac cycle. In the embodiment, the matching of the simulated aortic blood pressure to the sensed aortic blood pressure or the derivative thereof in the cardiac cycle is performed outside the time interval. The part outside the time interval may be the part during diastole of the cardiac cycle that is not affected by the heart assist device In one embodiment, the time interval during which the heart assist device affects the sensed aortic blood pressure is determined by monitoring the heart assist device (e.g. the pressure in the intra-aortic balloon). The heart assist device is a reliable information source for determining which part (timing, duration) of the sensed aortic blood pressure should be suppressed.

Instead of sensing the blood pressure in the aorta, blood pressure may be sensed in the left ventricle of the heart. In this embodiment, the sensed blood pressure is the pressure sensed in the left ventricle.

In one embodiment, the method comprises the step of matching the simulated aortic blood pressure to the blood pressure in the left ventricle of the heart at the time of the end of the cardiac cycle. The time of the end of the cardiac cycle, e.g. the end of the diastolic stage, may be measured from monitoring the steepest positive slope of the sensed blood pressure in the left ventricle of the heart.

In one embodiment, the method further comprises setting the derived blood flow to zero during a diastolic stage of the cardiac cycle. By setting the computed blood flow to zero in the diastolic stage before re-introducing the blood flow in the arterial model, a more accurate simulated aorta pressure is obtained (e.g. compensating for retarding blood flow effects when the blood pressure is sensed in the aorta)

In one embodiment, the arterial flow model comprises a Windkessel model and the values of the arterial flow parameters comprise at least a capacitor value $C_W$ associated with arterial compliance and a resistance value $R_p$ associated with peripheral resistance. The Windkessel model enables derivation of the blood flow from the sensed blood pressure or the derivative thereof and derivation of the simulated aortic blood pressure from the derived blood flow. Manipulation of the values of the Windkessel arterial flow parameters enables matching the simulation aortic blood pressure with a part of the sensed blood pressure or the derivative thereof.

The values of some of the arterial flow parameters of the Windkessel model are not necessarily manipulated for the matching operation. In one embodiment, the capacitor value is obtained using the modified aortic blood pressure over the cardiac cycle. The modified aortic blood pressure may be used in combination with the cross sectional area (CSA) of the aorta for deriving the capacitor value. The CSA may be determined using echo, conductance or other measurements. For this derivation, other information may be needed, such a patient data (e.g. age, gender, weight and/or height of the patient) and the density and/or conductivity of the blood may be used. If the Windkessel model includes the input impedance parameter, a value of this parameter may also be derived at this stage. The flow parameters may be derived in other manners, e.g. by using a fixed pressure value for the working point for the cardiac cycle on the relation between a cross-sectional area of the aorta and the modified aortic blood pressure.

The applicant has found that one parameter value that may be manipulated for the matching operation comprises the resistance value. Hence, in one embodiment, the step of manipulating the resistance value at least one time to match the simulated aortic blood pressure to the part of the sensed blood pressure in the cardiac cycle, wherein the part is preferably outside the time interval. As mentioned above, the matching process may be an iterative process, wherein the manipulated resistance value is used as an input for again deriving the blood flow from the modified aortic blood pressure from which a further simulated aortic blood flow is derived for matching with the sensed aortic blood flow. The number of iterations n may range from 2 to 10, preferably between 2 and 5. Good results have been obtained for n=3, 4, 5, 6 and 7.

In one embodiment, the initial resistance value corresponds to the resistance value obtained in a previous cardiac cycle, e.g. the preceding cardiac cycle.

As mentioned above, the processed output of the heart sensor may be used to as input for another device, such as a patient monitoring device or a heart assist device. Examples include:

outputting, e.g. displaying, the matched simulated aortic blood pressure over the cardiac cycle and/or characteristic values thereof;

outputting, e.g. displaying, the at least one manipulated value of the arterial flow parameters;

controlling a heart assist device using at least the at least one manipulated value of the arterial flow parameters;

determining a stroke volume of the heart using the used arterial flow parameters.

As will be appreciated by one skilled in the art, one or more steps of the present disclosure may be embodied as a system, a method or a computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Functions described in this disclosure may be implemented as an algorithm executed by a processor/microprocessor of a computer. Furthermore, aspects of the present disclosure may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium may include, but are not limited to, the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present invention, a computer readable storage medium may be any tangible medium that can contain, or store, a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present invention may be written in any combination of one or more programming languages, including an object oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the present invention. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor or a central processing unit (CPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

Embodiments of the present invention will be further illustrated with reference to the attached drawings, which schematically will show embodiments according to the invention. It will be understood that the present invention is not in any way restricted to these specific embodiments.

It is noted that the invention relates to all possible combinations of features recited in the claims.

BRIEF DESCRIPTION OF THE DRAWINGS

Aspects of the invention will be explained in greater detail by reference to exemplary embodiments shown in the drawings, in which:

FIG. 5 is a flow chart showing some steps of obtaining blood flow from the sensed aortic blood pressure and an arterial flow model;

FIG. 7 is a flow chart showing some steps of processing a heart sensor output comprising a sensed aortic pressure for a cardiac cycle wherein the heart is assisted by a heart assist device;

FIG. 11 is a flow chart showing some steps of processing a heart sensor output comprising a sensed aortic pressure for a cardiac cycle wherein the heart is not assisted by a heart assist device;

FIG. 13 is a flow chart showing some steps of processing a heart sensor output comprising a sensed blood pressure in the left ventricle of the heart, wherein the heart is not assisted by a heart assist device;

DETAILED DESCRIPTION OF THE DRAWINGS

Figure 1C:
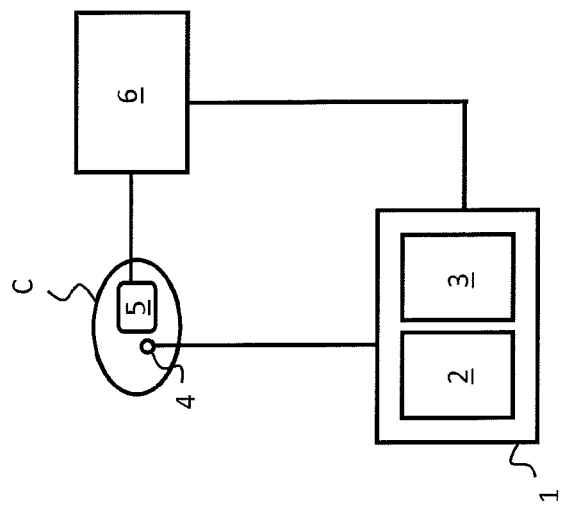
FIGS. 1A-1C show schematic diagrams of computer systems configured for obtaining and processing heart sensor outputs according to embodiments of the invention.
Figure 1B:
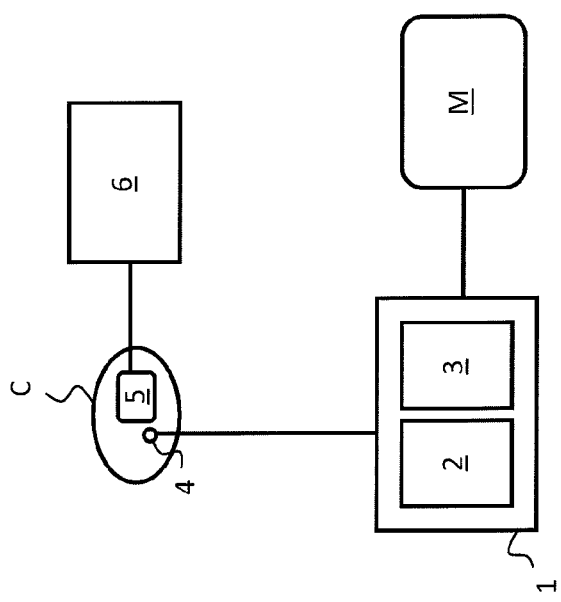
Figure 1A:
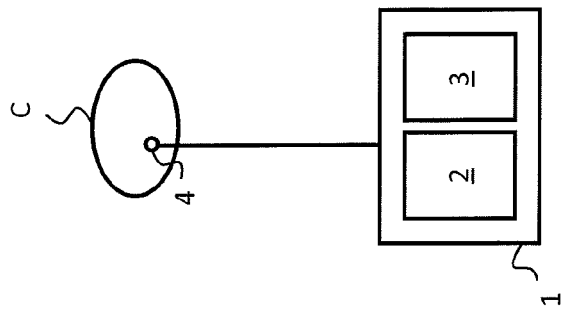
Figure 8:
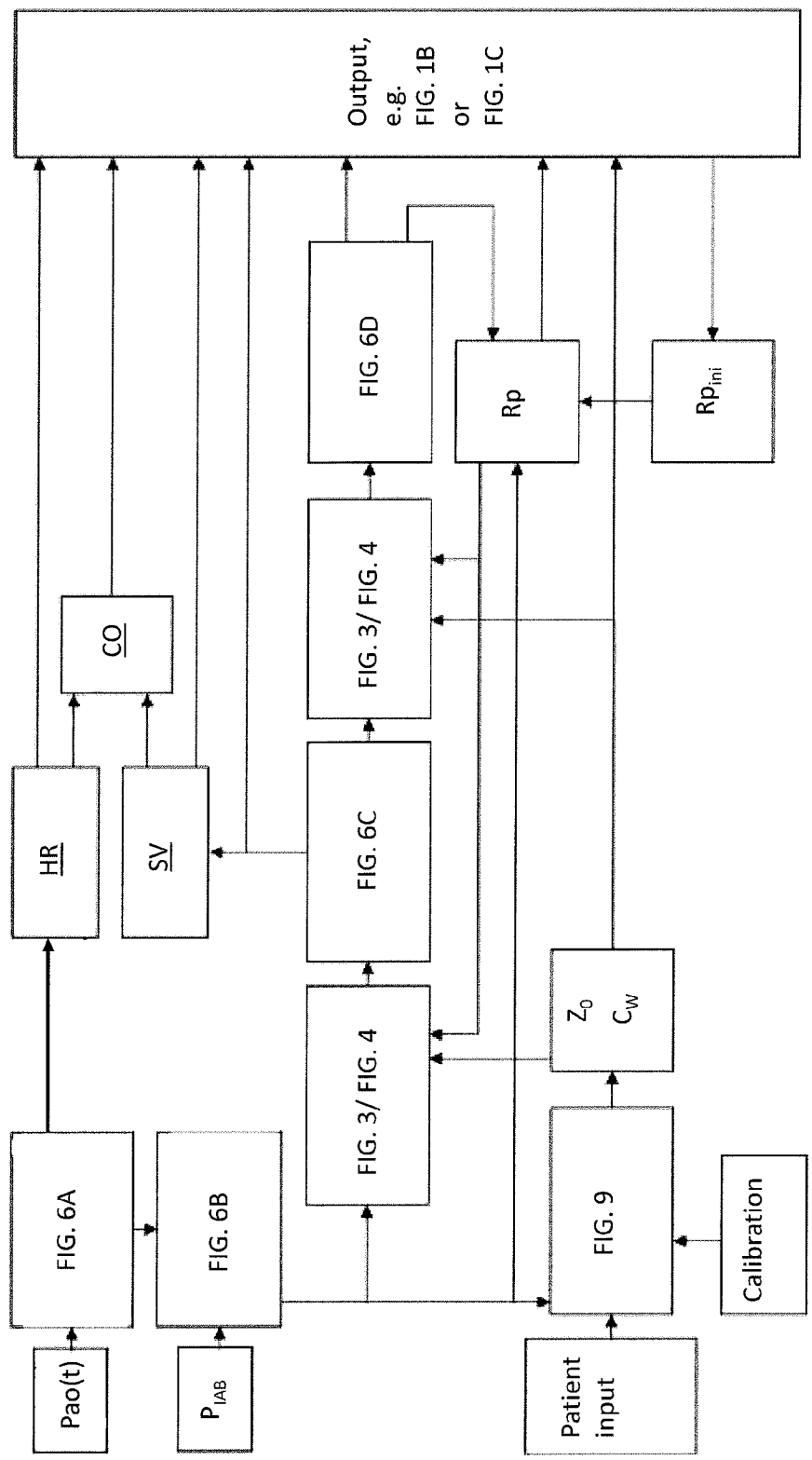
FIG. 8 is a schematic illustration of stages in a computer system for performing an embodiment of the heart sensor output processing method of FIG. 7.
Figure 14:
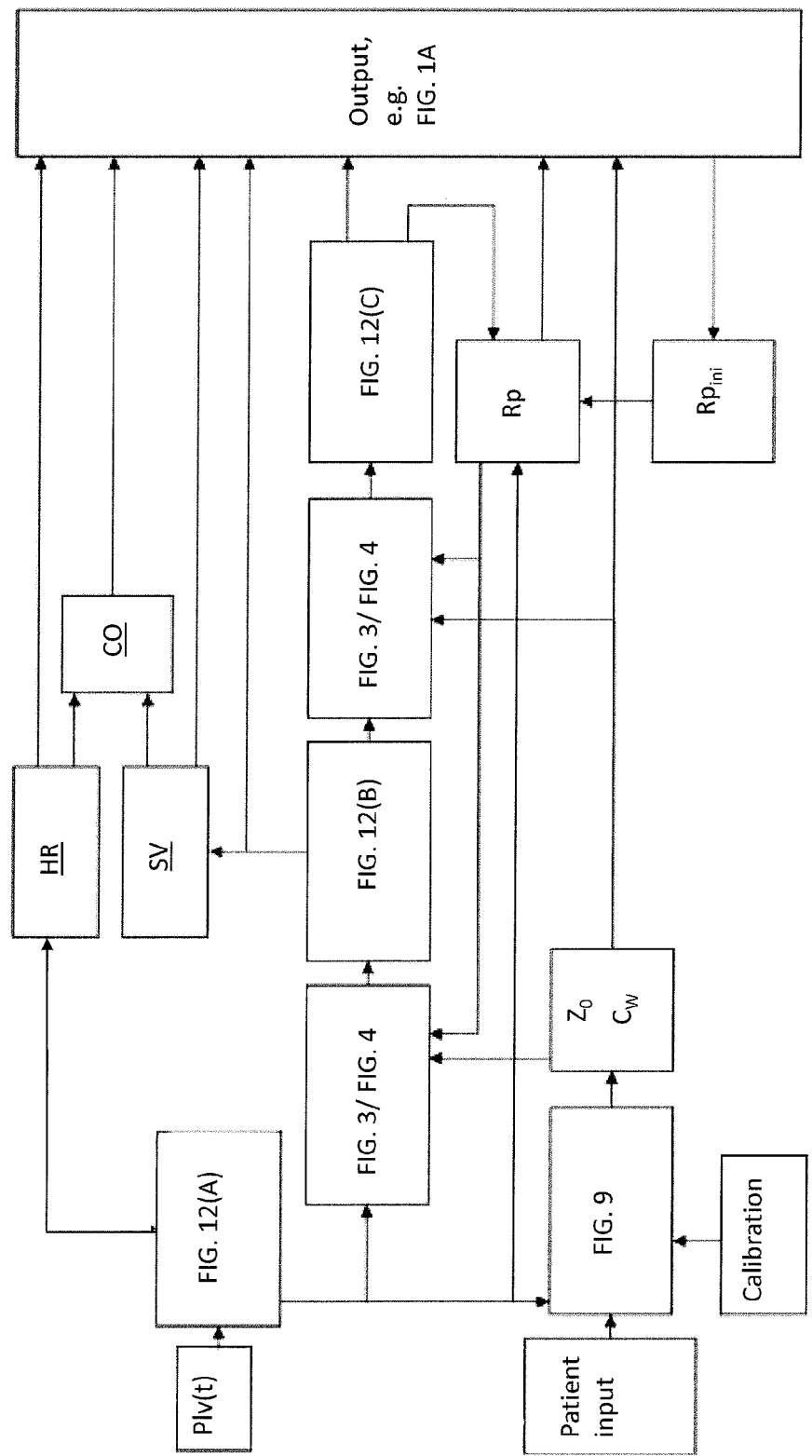
FIG. 14 is a schematic illustration of stages in a computer system for performing an embodiment of the heart sensor output processing method of FIG. 13.
Figure 15:
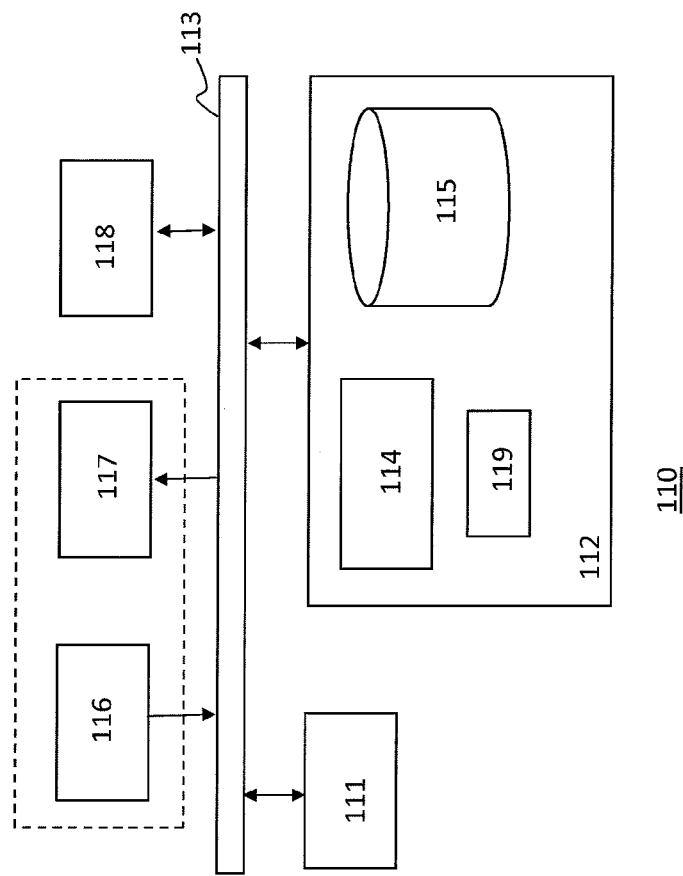
FIG. 15 is a schematic block diagram of a general system, such as the computer system.

FIGS. 1A-1C show schematic diagrams of computer systems 1 configured for obtaining and processing heart sensor outputs according to embodiments of the invention. Each of the computer systems comprises at least a memory 2 and a processor 3 configured for executing instructions for processing the heart sensor output as disclosed herein. FIGS. 8, 14 and 15 and the corresponding description provide further details on the computer system 1.

FIG. 1A depicts a heart related cavity C, e.g. an aorta or a ventricle of the heart, wherein a heart sensor 4 is inserted. The heart sensor 4 continuously senses the pressure Pao(t) in the aorta or the pressure Plv(t) in the left ventricle of the heart as a function of time t in order to obtain a sensed blood pressure. The sensed blood pressure is output to the computer system 1 for further processing.

FIG. 1B depicts a similar situation wherein computer system 1 is connected to a monitor M for displaying processing results. Monitor M may be integrated with the computer system 1 or may be positioned at a distance from computer system 1. A heart assist device 5, e.g. an intra-aorta balloon IAB may be placed in the cavity C. Heart assist device 5 is controlled by heart assist controller 6. Heart assist controller 6 may contain a pressure generator providing a pressure $P_{IAB}$ for an IAB. The heart assist controller 6, or a part thereof, may be integrated with the computer system 1.

In the arrangement of FIG. 1C, the computer system 1 is connected with the heart assist controller 6. Computer system 1 may receive information from the heart assist controller 6 and processing results from computer system 1 may be used for controlling heart assist controller 6. A more detailed description of such an arrangement is described below with reference to FIG. 10. Again, heart assist controller 6 may be integrated with the computer system 1.

The aortic blood pressure Pao may be measured with any catheter placed in the ascending part of the aorta C but preferably with a high fidelity pressure transducer mounted on the top of the catheter or positioned in front of the catheter.

Rather than measuring Pao in the aorta, any other signal or arterial pressure may be used that is proportional to or can be converted to aorta pressure Pao, for instance the pressure measured in the brachial artery or other more peripheral pressures. Any needed scaling or conversion may then be done at any or all of several points needed to perform the calculation as described in the invention. The measured signal is equal or at has at least a known relationship to the aorta pressure Pao over the time interval of interest. An example of such signal may be the pressure Plv measured in the left ventricle of the heart, as will be described further with reference to FIGS. 12-14

Figure 2:
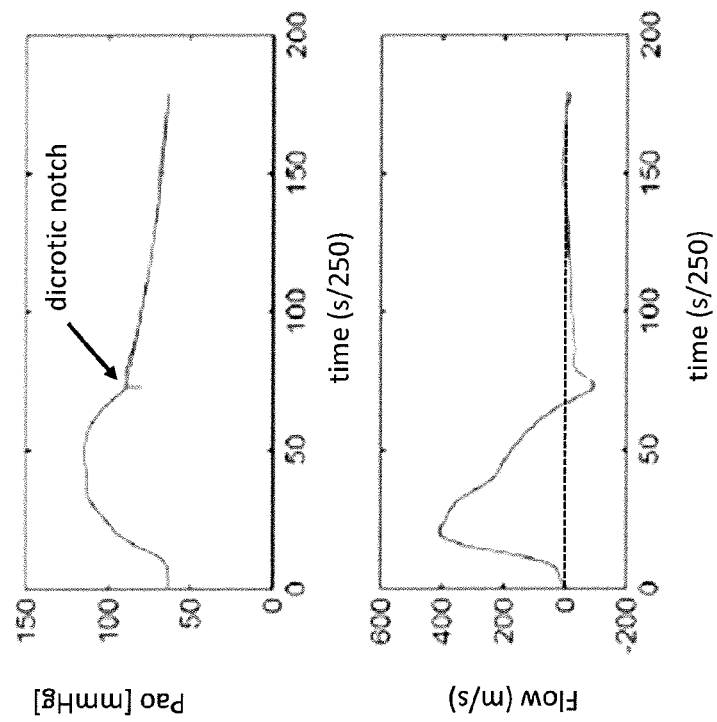
FIG. 2 shows diagrams of a sensed aortic blood pressure and blood flow derived from the sensed aortic blood pressure for a heartbeat.

The top diagram of FIG. 2 depicts the sensed aortic pressure Pao over a single heartbeat, i.e. a cardiac cycle. Throughout the cardiac cycle, the blood pressure increases and decreases. Each cardiac cycle contains two major stages, viz. a systolic stage and a diastolic stage.

The systolic stage relates to the contraction phase of the heart. The cardiac diastolic stage is the period of time when the heart relaxes in preparation of refilling with circulating blood. The graph of aortic pressure throughout the cardiac cycle displays a small dip, referred to as the dicrotic notch, which coincides with the aortic valve closure. The dip in the graph is immediately followed by a brief rise (the "dicrotic wave") and then a gradual decline. Just as the ventricles enter into diastole, the brief reversal of flow from the aorta back towards the left ventricle causes the aortic valves to shut. This results in the slight increase in aortic pressure caused by the elastic recoil of the semilunar valves and aorta From the sensed aortic pressure Pao, it is common to derive the blood flow corresponding to the sensed aortic pressure. As example of the blood flow during the cardiac cycle is shown in the lower diagram of FIG. 2.

One known manner to derive blood flow is by means of an arterial flow model, e.g. the Windkessel model. The Windkessel model models anatomical components, such as the left heart ventricle, the aortic valve, the arterial vascular system and the peripheral flow pathway. These components are represented by arterial flow parameters.

The analog model that represents such a system has a single active flow parameter (capacitor $C_W$) and a single passive flow parameter (resistance) in combination with a diode D representing the aortic valve. Such a system only accounts for the single exponential decay in arterial pressure Pao(t) during the diastolic phase of the heartbeat.

Figure 3:
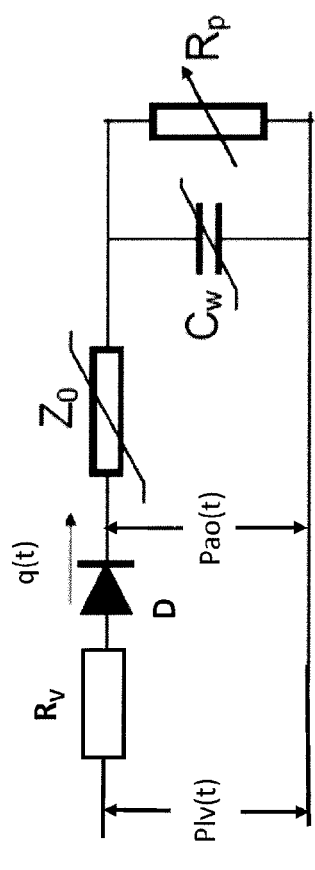
FIGS. 3 and 4 show diagrams of arterial flow Windkessel models.

An improvement to this two-element model is a three element model, as shown in FIG. 3, that results in a better description of the systolic pressure and diastolic pressure decay measured in the aorta of a human being. In order to derive the flow q(t), the model contains two active elements, viz. a pressure dependent compliance represented by a capacitor $C_W$ and a pressure dependent inertia of blood represented by a characteristic impedance $Z_0$ and one passive element being systemic vascular resistance represented by $R_P$. An example of using this model for controlling heart assist device is disclosed in US 2004/0059183.

Recently, it has been found that that the backpressure for blood flow to the peripheral circulation is not equal to zero as is assumed in all known existing three element Windkessel models. The present disclosure now proposes to implement this backpressure in the Windkessel model by a Zener diode $Z_D$ as shown in FIG. 4.

The Zener diode $Z_D$ accounts for the backpressure of the blood flow described as a waterfall phenomenon by Maas et al. The backpressure may vary between 0 and 50 mmHg.

Inclusion of the backpressure in the Windkessel model improves the accuracy in deriving blood flow q(t).

Figure 4:
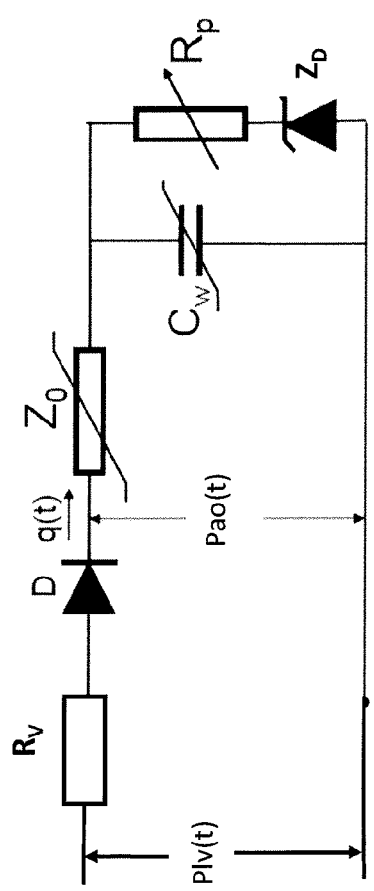

The Windkessel models as shown in FIGS. 3 and 4 may also be used when the left ventricle pressure Plv(t) is sensed. If Plv(t) is sensed, a flow resistance $R_v$ is used to represent the flow resistance of the aorta valve between the left ventricle and the aorta. Values of $R_v$ are known from literature.

FIG. 5 illustrates some steps in deriving blood flow q(t). In step S1, the aortic pressure Pao(t) is sensed using a pressure sensor 4 in the aorta. Similarly, the left ventricle pressure Plv(t) may be sensed in the left ventricle of the heart.

In step S2, the Windkessel arterial flow model including Zener diode $Z_D$ of FIG. 4 is applied. In step S3, the blood flow q(t) is obtained. An example of a computer system 1 using the Windkessel model to derive blood flow q(t) from sensed aortic pressure Pao(t) or the sensed left ventricle pressure Plv(t) is shown in FIG. 1A.

One embodiment of the present disclosure pertains to sensing aortic blood pressure wherein the aortic blood pressure is influenced by a heart assist device. This embodiment will now be described with reference to FIGS. 6A-6D and FIGS. 7-10.

FIG. 2 depicted a measurement of the aortic blood pressure Pao(t) for a single cardiac cycle in the situation of FIG. 1A. As mentioned previously, the operation of a heart assist device 6 will seriously affect the pressure measurement.

Figure 6C:
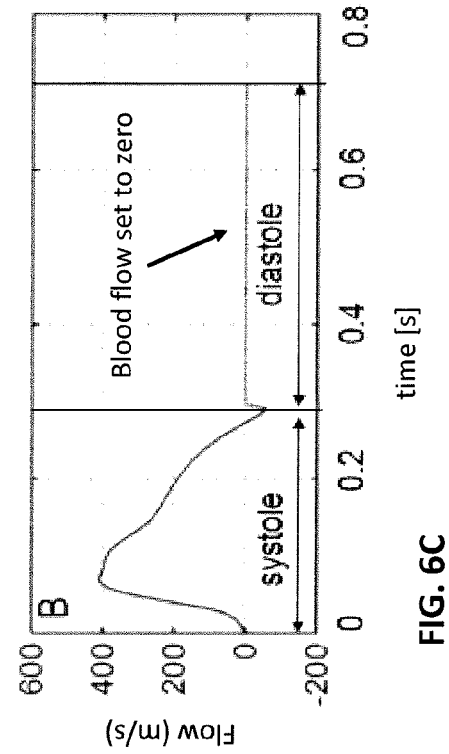
FIGS. 6A-6D show plots of one cardiac cycle of (A) a sensed aortic blood pressure, (B) a modified aortic blood pressure, (C) a blood flow derived from the modified aortic blood pressure and (D) a simulated aortic blood pressure, wherein the heart is assisted by a heart assist device.
Figure 6D:
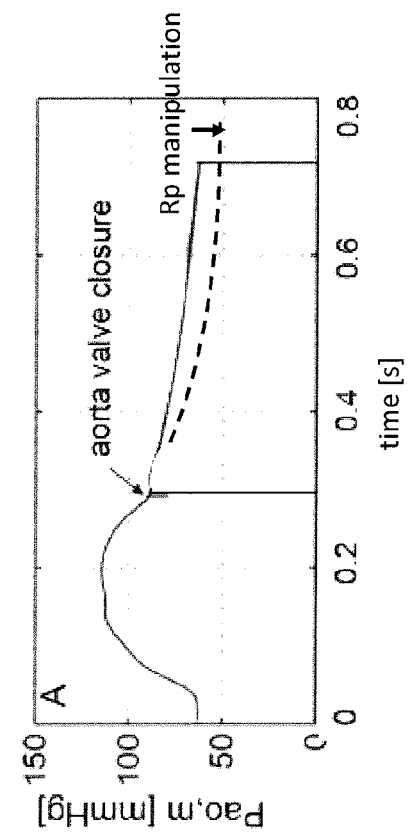
Figure 6A:
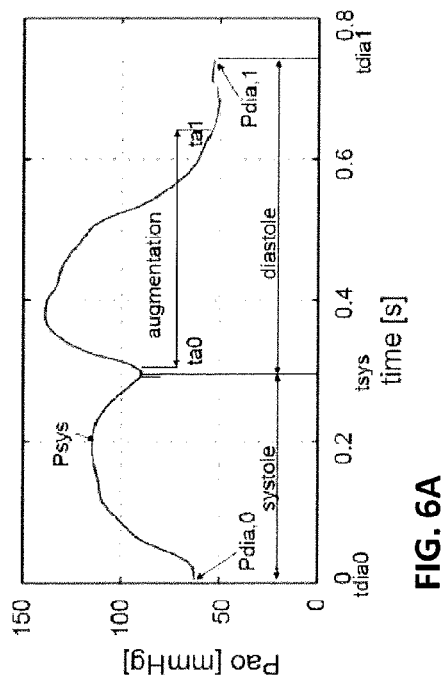

FIG. 6A depicts a schematic diagram of sensed aortic blood pressure Pao for a single cardiac cycle, wherein the heart assist device 5 comprises an intra-aortic balloon IAB. Clearly, the IAB influences the pressure during the diastolic stage of the cardiac cycle.

In normal inflation-deflation timing, balloon inflation occurs at the onset of diastole, after aortic valve closure; deflation occurs during the latter part of the diastole, just before the aortic valve opens. If properly timed, the inflation point lies at or slightly after the dicrotic notch.

In particular, the sensing of the aortic pressure for the cardiac cycle comprises the systolic stage and the diastolic stage. At the beginning of the systolic stage, the sensed pressure corresponds to the pressure at the end of the diastolic stage of the previous cardiac cycle, i.e. Pdia0 at time tdia0. At the end of the cardiac cycle, the sensed pressure corresponds to Pdia1 at time tdia1. The systolic stage of the cardiac cycle spans the time interval from tdia0 to tsys with Psys being the highest aortic pressure during this interval. The diastolic stage spans a time interval from tsys to tdia1. The time interval of the cardiac cycle during which the IAB influences the aortic pressure is indicated with "augmentation" in FIG. 6A and spans a time interval from ta0 (just after the dicrotic notch) to ta1. During the diastolic stage, the pressure during the part ta1 to tdia1 is not augmented by the IAB.

The sensing or derivation of the aortic pressure as a function of time is indicated as step S10 in FIG. 7 and indicated in the top left corner of the system diagram of FIG. 8. The heart rate HR can be calculated as 60/(tdia1−tdia0).

Figure 6B:
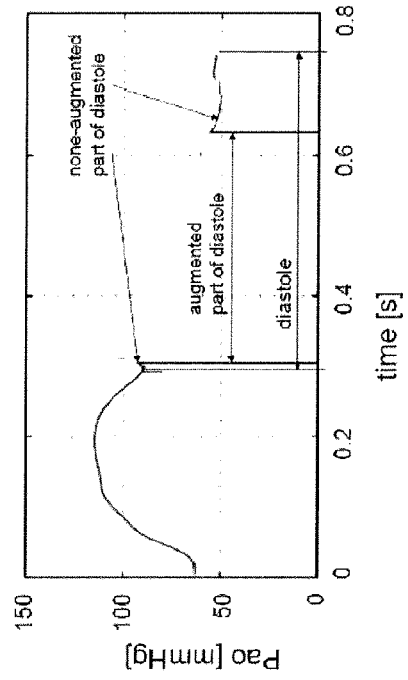

In a second step S11, a modified aortic pressure Pao is obtained over the cardiac cycle, as shown in FIG. 6B. Modified aortic pressure Pao is derived by processing the sensed aortic pressure Pao in computer system 1. In particular, computer system 1 may suppress the sensed aortic blood pressure during the time interval of the cardiac cycle, e.g. by inhibiting a value or setting the value of Pao to zero over the time interval during which Pao is augmented, i.e. of time interval ta0-ta1 during the diastolic stage. The heart assist device is a reliable information source for determining which part (timing, duration) of the sensed aortic blood pressure should be suppressed.

Various direct and indirect methods may be used to identify the time interval ta0-ta1. In one embodiment, the pressure $P_{IAB}$ is measured and correlated with the time interval ta0-ta1. Once the time interval ta0-ta1 is determined, the modified aortic blood pressure can be obtained.

In a third step, S12, blood flow q(t) is obtained from the modified aortic pressure using an arterial flow model as shown in FIGS. 3 and 4. An arterial flow model comprises a model providing a relationship between arterial pressure and blood flow.

When the Windkessel model described above with reference to FIG. 3 is taken for the arterial flow model, the following mathematical equation applies:

$$\frac{1+Z_0}{R_P}q(t) + Z_0 C_W \frac{dq(t)}{dt} = \frac{1}{R_P} Pao(t) + C_W \frac{dPao(t)}{dt} \quad (1)$$

wherein dq(t)/dt and dPao(t)/dt are first order time derivatives of the blood flow q(t) and the sensed aortic blood pressure Pao(t) and $Z_0$, $C_W$ and $R_P$ are arterial flow parameters.

When the Windkessel model of FIG. 4 is used, the following relation applies:

$$\frac{1+Z_0}{R_P}q(t) + Z_0 C_W \frac{dq(t)}{dt} = \frac{1}{R_P}(Pao(t) - P_{Z_D}) + C_W \frac{dPao(t)}{dt} \quad (2)$$

The modified aortic blood pressure may be used as input for the calculation of flow parameters $Z_0$ and $C_W$ as shown in the bottom-left corner of FIG. 8. Time varying $Z_0$ and $C_W$ depend on the cross-sectional area CSA of the aorta and may e.g. be estimated using the arctangent model of Langewouters et al, J. Biomechanics (1984) 17, 425-434.

Figure 9:
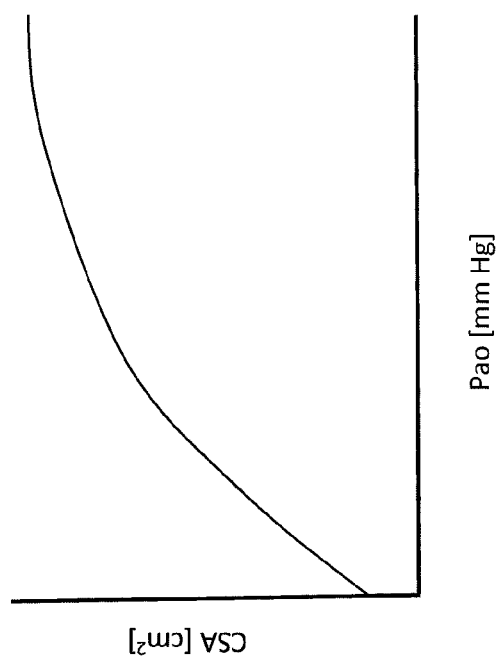
FIG. 9 shows an arctangent pressure/CSA relationship for a particular patient.

Further input information may comprise patient related input (age, gender, height, weight) and a calibration factor. This information may be used to obtain a dependency of the cross-sectional area CSA of the aorta and the pressure Pao(t), as shown in FIG. 9. One way of obtaining this dependency is described in US 2008/0208062. From the working point Pao(t) on the CSA vs. pressure relationship, a pressure dependent value of $Z_0$ and $C_W$ is obtained, as was described e.g. in US 2008/0208062.

Murgo and Westerhof in Circ. Res. (1984) 54: 666-673, derive the characteristic input resistance $Z_0$ as:

$$Z_0 = \sqrt{\frac{\rho}{(CSA \cdot C'_W)}} \quad (3)$$

where, ρ is the density of blood, CSA is the cross sectional area of the aorta at pressure Pao and $C'_W$ is the value of the first derivative of the pressure/CSA relationship at a measured pressure, Pao.

The arterial compliance $C_W$ is found by multiplying $C'_W$ with an effective length of the arterial system of the patient. For effective length usually half the height of a patient is chosen. $C_W$ decreases substantially when aortic pressure increases. This non-linear behavior of the aortic wall may be a major source of error if not taken into account in the manner as described above.

The flow parameters $Z_0$ and $C_W$ may be derived in other manners, e.g. by using a fixed pressure value for the working point on the relation between a cross-sectional area of the aorta and the modified aortic blood pressure. One example comprises deriving a mean pressure value by calculating (systolic pressure+2*diastolic pressure)/3 as the working point and calculating fixed values for $Z_0$ and $C_W$.

Aortic flow parameter $R_P$ may be taken from the previous cardiac cycle, $Rp_{ini}$, as shown in FIG. 8. The value of Rp can be computed by assuming that the total amount of blood that flows into the arterial vascular system during a cardiac cycle, or over a number of cycles, will also flows out of said arterial vascular system again. In other words, q(t)=0 is the value of q(t) to arrive at the end of a cardiac cycle.

Using the thus determined values for the aortic flow parameters, a value for blood flow, q(t), can be derived by means of equation (1) or (2). The closing time of the heart valve can be accurately derived from the blood flow rate that has been computed by determining the time of the first local minimum after the beginning of the ejection phase of the heart.

The blood flow derived from the modified aortic pressure, the arterial blood flow model and the determined arterial flow parameters is shown in FIG. 6C. The derived blood flow is set zero during the diastolic stage to account for retarding effects.

From the simulated blood flow, a stroke volume SV may be determined as shown in FIG. 8. By multiplying the thus obtained stroke volume SV with the heart rate HR, the cardiac output CO can be derived as also shown in FIG. 8. Heart rate HR and/or cardiac output CO may be output as shown in FIG. 8. The output HR and CO may be shown on monitor M of FIG. 1B.

Then, in step S13, the simulated aortic pressure over a cardiac cycle is derived from the blood flow obtained in step S12. The simulated aortic blood pressure is shown by the solid curve in FIG. 6D.

The simulated aortic blood pressure may be obtained from the blood flow derived in step S12 using again equation (1) or (2). This is shown in FIG. 8. The same arterial flow parameters $Z_0$, $C_W$ and Rp may be used in this step.

In step S14, the simulated aortic blood pressure may then be matched to a part of the sensed aortic blood pressure in the cardiac cycle by manipulating at least one of the values for the arterial flow parameters of the arterial flow model. The part outside the time interval may be the part during diastole of the cardiac cycle that is not affected by the heart assist device, i.e. the part from ta1 and tdia1.

One arterial flow parameter that may be manipulated is Rp. The result of manipulating Rp to match the simulated aortic blood pressure to the sensed aortic blood pressure is shown by the dashed line in FIG. 6D. As can be observed from comparing the dashed line in FIG. 6D with the non-augmented part from FIG. 6B, manipulating Rp results in matching the curves in the part during diastole of the cardiac cycle that is not affected by the heart assist device. The matching operation involves minimizing the difference between the simulated and the sensed aortic blood pressure during the part outside the time interval, i.e. between ta1 and tdia1

FIG. 8 indicates that the matching process may be an iterative process, wherein the manipulated resistance value is fed back to be used as an input for again deriving the blood flow in step S12 from the modified aortic blood pressure from which a further simulated aortic blood flow in step S13 is derived for matching with the sensed aortic blood flow in step S14. The number of iterations n may range from 2 to 10, preferably between 2 and 5. Good results have been obtained for n=3.

The result of the processing of the sensed aortic blood pressure may be used as an input for another device, e.g. for controlling another device, such as a patient monitoring device or a heart assist device. For example, a beat-to-beat aortic pressure curve may be obtained that is compensated for the effect of the heart assist device. Furthermore, the variation of the value of one or more arterial flow parameters can be monitored. Both may be shown on monitor M connected to the computer system 1 in FIG. 1B.

In another embodiment, after optimization, beat-to-beat stroke volume SV is calculated by integration of the systolic part of the simulated aortic blood flow shown in FIG. 6C. Cardiac output CO is found by multiplying stroke volume SV with heart rate HR which is derived from the sensed aortic pressure shown in FIG. 6A.

Figure 10:
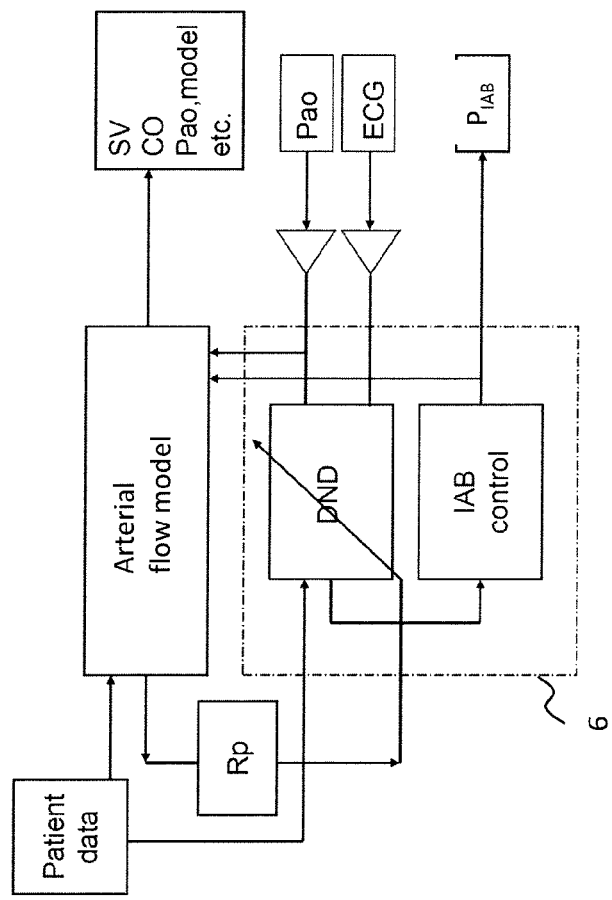
FIG. 10 is a schematic illustration of a system using the computer system to control a heart assist control device.

In another embodiment, the arterial flow parameters of the Windkessel model as determined, possibly iteratively, may be used to control the heart assist control device 6 as input of dicrotic notch detection (DND) algorithms in a system as shown in FIG. 10. In such an embodiment, stopping of the heart assist device 5 is not required.

FIG. 10 shows the main components of a system that implements this approach. In a practical clinical implementation with an IAB 5 and a IAB control device 6 device the aortic pressure Pao(t) is sensed from high fidelity pressure transducer positioned at the top of an IAB catheter. The sensed aortic pressure as shown in FIG. 6A is fed to the Windkessel model and to the DND part of the IAB control device 6. The IAB pressure Piab generated by the IAB control device 6 is also inputted to the Windkessel model as shown in FIG. 8. Furthermore, patient data (e.g. age, gender, weight and length of the patient) is used as input for both the Windkessel model as well as the DND module. After processing the sensed aortic blood pressure as described above, the output of Windkessel parameter Rp is used as input for the DND algorithm. In this way all three parameters (Rp, $C_W$ and $Z_0$) for executing the DND module are obtained and the IAB control device 6 does not need to be interrupted from working to derive parameter Rp as in the state of the art.

With the beat-to-beat optimized value for parameter Rp the correct model simulated time varying aortic blood flow is estimated. From this aortic blood flow pattern the moment of aortic valve closure is determined at the first local minimum in the aortic flow signal after aortic peak flow as is described in U.S. Pat. No. 6,258,035. U.S. Pat. No. 7,169,109 describes a method to predict the moment of aortic valve closure 0-100 milliseconds ahead in time. This prediction method is used to set the time moment of inflation of the IAB. A more precise determination of Rp, as described above results in a better model estimation of the time varying aortic blood flow and improves prediction of the time moment for inflation of IAB.

A precise determination of the systolic stage (i.e. the time interval between start of the beat and time of aorta valve closure) and the diastolic stage (i.e. the time interval between aortic valve closure and start of the next heart beat) of the cardiac cycle enables judgment of the quality of IABP timing. The IAB must be inflated effectively shortly after start of diastole and emptied effectively before the end of diastole. A measure of actual IAB volume can be derived from several signals inside the IABP system, for instance the pressure $P_{IAB}$ in the tubing of the IAB catheter. The applied pressure for the IAB may be earlier in time than the increase of volume of the IAB. Therefore, with $P_{IAB}$ as time reference signal, a too early inflation may be detected if the start of balloon inflation is x milliseconds ahead of aorta valve closure. The value of x depends on the mechanical properties of the IAB catheter and IAB itself. Similar, with $P_{IAB}$ switching from a positive value to a negative value to deflate the balloon does not mean that the balloon is emptied instantaneously. Therefore, a too late deflation of the balloon is detected if the moment of $P_{IAB}$ going from a positive value to a negative pressure is less than y millisecond ahead of the end of diastole. The value of y depends on the mechanical properties of the IAB catheter and IAB itself.

Whereas the method disclosed above involves the use of a heart assist device 5, the method may also be used in the absence of a heart assist device 5 or for a cardiac cycle wherein the heart assist device is not operative. The latter case is encountered, e.g. wherein the heart assist device does not assist every single heart beat (i.e. mode 1:1), but every other heart beat (mode 1:2) or every third heart beat (mode 1:3), etc. The heart assist device may also be deactivated for a certain time period to monitor the performance of the heart without the heart assist device 5 being operative. The method of processing the heart sensor output operates with and without the heart assist device being present or operative.

FIG. 11 is a flow chart showing some steps of processing a heart sensor output comprising a sensed aortic pressure for a cardiac cycle wherein the heart is not assisted by a heart assist device 5. Indeed, as can be observed by comparing FIGS. 7 and 11, the steps S10-S14 are identical. The only difference is that the sensed aortic pressure Pao(t) does not contain a contribution from the heart assist device 5 in the diastolic stage of the heart cycle as shown in FIG. 6A but instead would sense an aortic pressure resembling FIG. 2, upper diagram.

As mentioned several times, the heart related cavity C wherein the pressure is sensed may involve the left ventricle of the heart. Below, it will be described how the left ventricle pressure Plv(t) may be sensed in order to derive the aorta pressure Pao(t) and, further, to obtain a processing output.

Figure 12:
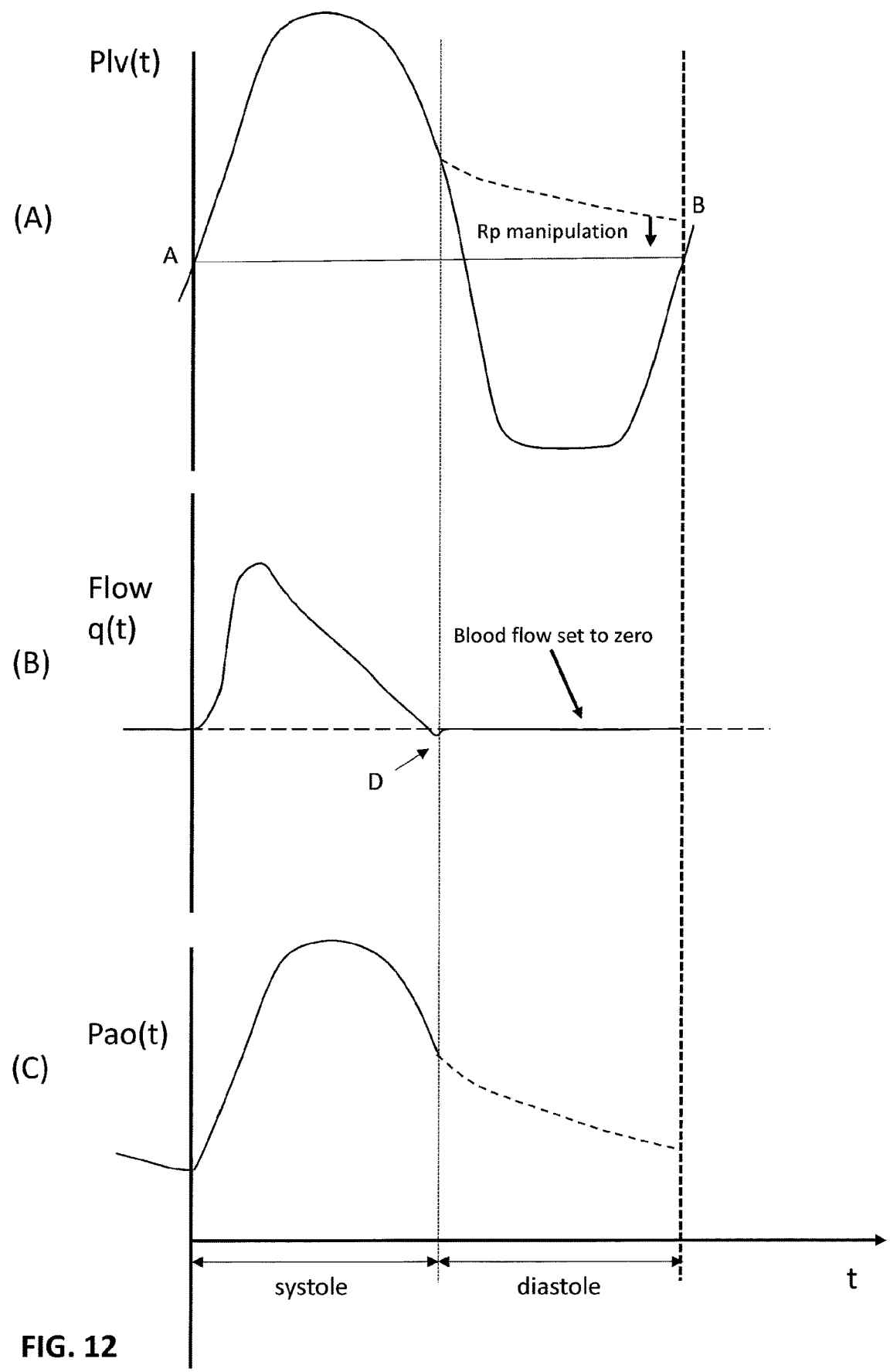
FIG. 12 shows schematic drawings of one cardiac cycle of (A) a sensed blood pressure in the left ventricle of the heart, (B) a blood flow derived from the sensed blood pressure in the left ventricle of the heart and (C) a simulated aortic blood pressure, wherein the heart is not assisted by a heart assist device.

FIG. 12 shows schematic drawings of one cardiac cycle of (A) a sensed blood pressure Plv(t) in the left ventricle of the heart, (B) a blood flow derived from the sensed blood pressure in the left ventricle of the heart and (C) a simulated aortic blood pressure, wherein the heart is not assisted by a heart assist device.

FIG. 13 is a flow chart showing some steps of processing a heart sensor output comprising a sensed blood pressure in the left ventricle of the heart, wherein the heart is not assisted by a heart assist device;

FIG. 14 is a schematic illustration of stages in a computer system for performing an embodiment of the heart sensor output processing method of FIG. 13.

In step S20, the left ventricle blood pressure is sensed and results in a sensed blood pressure vs. time diagram as shown in FIG. 12A.

A cardiac cycle may be found from the left ventricle pressure Plv(t) by detecting the maximal positive first derivative dPlv(t)/dt in the sensed pressure signal.

In step S21, the blood flow q(t) is derived from the left ventricle pressure Plv(t) using an arterial flow model, e.g. a Windkessel model as shown in FIG. 3 or 4. The initial values of the arterial flow model parameters, $C_W$, $Z_0$, $R_p$ and $R_v$ (and $Z_D$ in case of FIG. 4) may be used as calculated for previous cardiac cycles. From the derived blood flow, the transition point from the systolic stage to the diastolic stage in the cardiac cycle may be determined by determining the first local minimum, as described in US 2004/0059183. This is indicated as point D in FIG. 12(B). Once the diastolic stage has been determined between points D and B, the blood flow q(t) is set to zero for the diastolic stage.

In step S22, the simulated aortic blood pressure is derived by reversely using the arterial flow model with the blood flow as derived and modified (i.e. set to zero for the diastolic stage) in step S21. This is shown in FIG. 12(C). For the diastolic stage (started at point D where the aorta valve closes), the dashed line is obtained in step S23, wherein the end diastolic value of the simulated aortic pressure is matched with the value of sensed left ventricle pressure at point B by manipulating at least one of the arterial flow parameters, particularly $R_p$. Matching may be performed iteratively, for example n times, wherein n ranges from 3-7, e.g. 3, 4, 5, 6 or 7 times, within a cardiac cycle.

As shown in FIG. 14, the output may be the simulated aorta pressure Pao(t), the derived blood flow, the stroke volume SV, the cardiac output CO, the arterial flow parameters, etc. FIG. 15 is a schematic block diagram of a general system, such as the computer system 1.

As shown in FIG. 15, the data processing system 110 may include at least one processor 111 coupled to memory elements 112 through a system bus 113. As such, the data processing system may store program code within memory elements 112. Further, the processor 111 may execute the program code accessed from the memory elements 112 via a system bus 113. In one aspect, the data processing system may be implemented as a computer that is suitable for storing and/or executing program code. It should be appreciated, however, that the data processing system 110 may be implemented in the form of any system including a processor and a memory that is capable of performing the functions described within this specification.

The memory elements 112 may include one or more physical memory devices such as, for example, local memory 114 and one or more bulk storage devices 115. The local memory may refer to random access memory or other non-persistent memory device(s) generally used during actual execution of the program code. A bulk storage device may be implemented as a hard drive or other persistent data storage device. The processing system 110 may also include one or more cache memories (not shown) that provide temporary storage of at least some program code in order to reduce the number of times program code must be retrieved from the bulk storage device 115 during execution.

Input/output (I/O) devices depicted as an input device 116 and an output device 117 optionally can be coupled to the data processing system. Examples of input devices may include, but are not limited to, a keyboard, a pointing device such as a mouse, or the like. Examples of output devices may include, but are not limited to, a monitor or a display, speakers, or the like. Input and/or output devices may be coupled to the data processing system either directly or through intervening I/O controllers.

In an embodiment, the input and the output devices may be implemented as a combined input/output device (illustrated in FIG. 15 with a dashed line surrounding the input device 116 and the output device 117). An example of such a combined device is a touch sensitive display, also sometimes referred to as a "touch screen display" or simply "touch screen". In such an embodiment, input to the device may be provided by a movement of a physical object, such as e.g. a stylus or a finger of a user, on or near the touch screen display.

A network adapter 118 may also be coupled to the data processing system to enable it to become coupled to other systems, computer systems, remote network devices, and/or remote storage devices through intervening private or public networks. The network adapter may comprise a data receiver for receiving data that is transmitted by said systems, devices and/or networks to the data processing system 110, and a data transmitter for transmitting data from the data processing system 110 to said systems, devices and/or networks. Modems, cable modems, and Ethernet cards are examples of different types of network adapter that may be used with the data processing system 110.

As pictured in FIG. 15, the memory elements 112 may store an application 119. In various embodiments, the application 119 may be stored in the local memory 114, the one or more bulk storage devices 115, or apart from the local memory and the bulk storage devices. It should be appreciated that the data processing system 110 may further execute an operating system (not shown in FIG. 11) that can facilitate execution of the application 119. The application 119, being implemented in the form of executable program code, can be executed by the data processing system 110, e.g., by the processor 111. Responsive to executing the application, the data processing system 110 may be configured to perform one or more operations or method steps described herein.

In one aspect of the present invention, the data processing system 110 may represent a computer system 1 as disclosed herein.

Various embodiments of the invention may be implemented as a program product for use with a computer system, where the program(s) of the program product define functions of the embodiments (including the methods described herein). In one embodiment, the program(s) can be contained on a variety of non-transitory computer-readable storage media, where, as used herein, the expression "non-transitory computer readable storage media" comprises all computer-readable media, with the sole exception being a transitory, propagating signal. In another embodiment, the program(s) can be contained on a variety of transitory computer-readable storage media. Illustrative computer-readable storage media include, but are not limited to: (i) non-writable storage media (e.g., read-only memory devices within a computer such as CD-ROM disks readable by a CD-ROM drive, ROM chips or any type of solid-state non-volatile semiconductor memory) on which information is permanently stored; and (ii) writable storage media (e.g., flash memory, floppy disks within a diskette drive or hard-disk drive or any type of solid-state random-access semiconductor memory) on which alterable information is stored. The computer program may be run on the processor 111 described herein.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of embodiments of the present invention has been presented for purposes of illustration, but is not intended to be exhaustive or limited to the implementations in the form disclosed. Many modifications and variations will be apparent to those of ordinary skill in the art without departing from the scope and spirit of the present invention. The embodiments were chosen and described in order to best explain the principles and some practical applications of the present invention, and to enable others of ordinary skill in the art to understand the present invention for various embodiments with various modifications as are suited to the particular use contemplated.

The invention claimed is:

1. A method comprising:
receiving, at a computer system, a heart sensor output, the heart sensor output including a sensed blood pressure as sensed in a ventricle or in an aorta of a heart;
receiving, at the computer system, a heart assist information from an intra-aortic balloon pump, wherein the intra-aortic balloon pump affects the sensed blood pressure during a time interval extending over a portion of a cardiac cycle of the heart;
determining, using the computer system, a modified aortic blood pressure using the heart assist information from the intra-aortic balloon pump to determine the time interval during which the sensed blood pressure is affected by the intra-aortic balloon pump, and suppressing the sensed blood pressure over the time interval;
deriving, using the computer system, a blood flow from the modified aortic blood pressure by using an arterial flow model and setting one or more values for arterial flow parameters for the arterial flow model;
deriving, using the computer system, a simulated aortic blood pressure from the blood flow derived from the modified aortic blood pressure; and
matching, using the computer system, the simulated aortic blood pressure to a part of the sensed blood pressure in the cardiac cycle by manipulating at least one of the values for the arterial flow parameters of the arterial flow model; and controlling the intra-aortic balloon pump using at least the at least one manipulated value of the arterial flow parameters.

2. The method according to claim 1, wherein the sensed blood pressure is the sensed aortic blood pressure and the time interval is an inflation time interval that a balloon of the intra-aortic balloon pump is inflated, further comprising obtaining the derivative of the sensed aortic blood pressure by suppressing the sensed aortic blood pressure during the time interval.

3. The method according to claim 2, wherein the sensed aortic pressure is affected by the intra-aortic balloon pump during the time interval, further comprising matching the simulated aortic blood pressure to the sensed aortic blood pressure in the cardiac cycle outside the time interval.

4. The method according to claim 3, further comprising determining the time interval by monitoring the intra-aortic balloon pump.

5. The method according to claim 1, wherein the sensed blood pressure is the blood pressure in the left ventricle of the heart.

6. The method according to claim 5, further comprising matching the simulated aortic blood pressure to the blood pressure in the left ventricle of the heart at the end of the cardiac cycle.

7. The method according to claim 1, further comprising inhibiting use of the sensed blood pressure to derive blood flow and setting the derived blood flow to zero during the time interval and the sensed blood pressure is non-zero.

8. The method according to claim 1, wherein the arterial flow model comprises a Windkessel model and wherein the values of the arterial flow parameters comprise at least a capacitor value $C_W$ associated with arterial compliance and a resistance value $R_p$ associated with peripheral resistance.

9. The method according to claim 8, comprising determining the capacitor value using the sensed blood pressure or the derivative thereof over the cardiac cycle.

10. The method according to claim 8, wherein the capacitor value is further determined using a relation between a cross-sectional area of the aorta and the aortic blood pressure.

11. The method according to claim 8, comprising manipulating the resistance value at least one time to match the simulated aortic blood pressure to the part of the sensed blood pressure or the derivative thereof in the cardiac cycle.

12. The method according to claim 11, further comprising using an initial resistance value as obtained in a previous cardiac cycle.

13. The method according to claim 1, further comprising at least one of:
  outputting the matched simulated aortic blood pressure over the cardiac cycle and/or characteristic values thereof;
  outputting the at least one manipulated value of the arterial flow parameters;
  determining a stroke volume of the heart using the used arterial flow parameters.

14. A method comprising:
  receiving, at a computer system, a heart sensor output, the heart sensor output including a sensed blood pressure as sensed in a ventricle or in an aorta of a heart;
  receiving, at the computer system, a heart assist information from an intra-aortic balloon pump, wherein the intra-aortic balloon pump affects the sensed blood pressure during a time interval extending over a portion of a cardiac cycle of the heart;
  determining, using the computer system, a modified aortic blood pressure using the heart assist information from the intra-aortic balloon pump to determine the time interval during which the sensed blood pressure is affected by the intra-aortic balloon pump, and suppressing the sensed blood pressure over the time interval;
  deriving, using the computer system, a blood flow from the modified aortic blood pressure by using an arterial flow model and setting one or more values for arterial flow parameters for the arterial flow model;
  deriving, using the computer system, a simulated aortic blood pressure from the blood flow derived from the modified aortic blood pressure; and
  matching, using the computer system, the simulated aortic blood pressure to a part of the sensed blood pressure in the cardiac cycle by manipulating at least one of the values for the arterial flow parameters of the arterial flow model; and
  at least one of:
    outputting the matched simulated aortic blood pressure over the cardiac cycle and/or characteristic values thereof;
    outputting the at least one manipulated value of the arterial flow parameters;
    determining a stroke volume of the heart using the used arterial flow parameters.

15. The method according to claim 14, wherein the sensed blood pressure is the sensed aortic blood pressure and the time interval is an inflation time interval that a balloon of the intra-aortic balloon pump is inflated, further comprising obtaining the derivative of the sensed aortic blood pressure by suppressing the sensed aortic blood pressure during the time interval.

16. The method according to claim 15, wherein the sensed aortic pressure is affected by the intra-aortic balloon pump during the time interval, further comprising matching the simulated aortic blood pressure to the sensed aortic blood pressure in the cardiac cycle outside the time interval.

17. The method according to claim 16, further comprising determining the time interval by monitoring the intra-aortic balloon pump.

18. The method according to claim 14, wherein the sensed blood pressure is the blood pressure in the left ventricle of the heart.

19. The method according to claim 18, further comprising matching the simulated aortic blood pressure to the blood pressure in the left ventricle of the heart at the end of the cardiac cycle.

20. The method according to claim 14, further comprising setting the derived blood flow to zero during the time interval.

* * * * *